(12) United States Patent
Chung et al.

(10) Patent No.: US 12,161,518 B2
(45) Date of Patent: Dec. 10, 2024

(54) COMPOSITION FOR TREATING AND PREVENTING GINGIVOPERIODONTITIS OR PERI-IMPLANTITIS, AND INTERDENTAL BRUSH COATED WITH SAME

(71) Applicant: NIBEC CO., LTD., Chungcheongbuk-do (KR)

(72) Inventors: Chong-Pyoung Chung, Seoul (KR); Jue-Yeon Lee, Gyeonggi-do (KR)

(73) Assignee: Nibec Co., LTD., Chungcheongbuk-do (KR)

( * ) Notice: Subject to any disclaimer, the term of this patent is extended or adjusted under 35 U.S.C. 154(b) by 969 days.

(21) Appl. No.: 17/268,903

(22) PCT Filed: Aug. 17, 2018

(86) PCT No.: PCT/KR2018/009469
§ 371 (c)(1),
(2) Date: Feb. 16, 2021

(87) PCT Pub. No.: WO2020/036242
PCT Pub. Date: Feb. 20, 2020

(65) Prior Publication Data
US 2021/0267731 A1 Sep. 2, 2021

(51) Int. Cl.
| | |
|---|---|
| *A61C 13/08* | (2006.01) |
| *A61C 19/06* | (2006.01) |
| *A61K 38/17* | (2006.01) |
| *A61K 47/02* | (2006.01) |
| *A61K 47/18* | (2017.01) |
| *A61K 47/34* | (2017.01) |

(52) U.S. Cl.
CPC ............. *A61C 13/08* (2013.01); *A61C 19/06* (2013.01); *A61K 38/1729* (2013.01); *A61K 47/02* (2013.01); *A61K 47/183* (2013.01); *A61K 47/186* (2013.01); *A61K 47/34* (2013.01)

(58) Field of Classification Search
CPC .. A61K 38/1729; A61K 47/02; A61K 47/183; A61K 47/186; A61K 47/34; A61C 13/08; A61C 19/06
See application file for complete search history.

(56) References Cited

U.S. PATENT DOCUMENTS

| | | | | |
|---|---|---|---|---|
| 6,355,229 | B1 * | 3/2002 | Adamy | A61Q 11/00 424/440 |
| 8,974,805 | B2 * | 3/2015 | Chung | A61K 8/39 424/49 |
| 2012/0034280 | A1 * | 2/2012 | Cohen | A61K 31/4425 424/53 |
| 2013/0224128 | A1 | 8/2013 | Chung et al. | |

FOREIGN PATENT DOCUMENTS

| | | |
|---|---|---|
| CN | 101534823 A | 9/2009 |
| CN | 102006872 A | 4/2011 |
| CN | 103221031 A | 7/2013 |
| EP | 2415473 A1 | 2/2012 |
| EP | 2583684 A2 | 4/2013 |
| KR | 100621191 B1 | 9/2006 |
| KR | 100978822 B1 | 8/2010 |
| KR | 20110098685 A | 9/2011 |
| KR | 101249702 B1 | 4/2013 |
| KR | 20160123391 A | 10/2016 |
| KR | 20170046395 A | 5/2017 |
| KR | 20170075602 A | 7/2017 |
| WO | 2013052958 A2 | 4/2013 |

OTHER PUBLICATIONS

EESR issued on Mar. 11, 2022 for EP18930407.4.
Brogden, K. A. "Antimicrobial peptides: pore formers or metabolic inhibitors in bacteria", Nat. Rev. Microbiol., 3, Mar. 2005, 238-250.
Giacometti, A. et al., "Potential therapeutic role of cationic peptides in three experimental models of septic shock", Antimicrob. Agents Chemother., 46(7), Jul. 2002, 2132-2136.
Rosenfeld, Y. et al., "Endotoxin (lipopolysaccharide) neutralization by innate immunity host-defense peptides; Peptide properties and plausible modes of action", J. Biol. Chem., 281(3), Jan. 20, 2006, 1636-1643.
Scott, M. G. et al., "Interaction of cationic peptides with lipoteichoic acid and Gram-positive bacteria", Infect. Immun., 67(12), Dec. 1999, 6445-6453.
Sørensen, O. E. et al., "Antimicrobial peptides in innate immune responses", Contrib. Microbiol., 15, 2008, 61-77.
Search Report issued on Jul. 19, 2022 for the CN patent application No. 201880097769.6.
Translated Office Action issued on Jul. 25, 2022 for the CN patent application No. 201880097769.6.

* cited by examiner

*Primary Examiner* — Blessing M Fubara
(74) *Attorney, Agent, or Firm* — Elmore Patent Law Group, P.C.; Joseph C. Zucchero; Carolyn S. Elmore

(57) ABSTRACT

The present invention relates to a pharmaceutical composition for treating and preventing gingivoperiodontitis or peri-implantitis, comprising, as effective components, sodium ethylenediaminetetra acetate, cetylpyridinium chloride, octyl phenol ethoxylate, and sodium bicarbonate. The composition according to the present invention can effectively eliminate bacteria causing gingivoperiodontitis and peri-implantitis, thereby alleviating inflammation, and furthermore, an interdental brush coated with the composition is convenient to apply to gaps between teeth, dental implants, orthodontic appliances, etc. and thus can be used to treat and prevent gingivoperiodontitis and peri-implantitis conveniently at home.

9 Claims, 5 Drawing Sheets

Specification includes a Sequence Listing.

Composition effective for alleviating and preventing symptoms of gingivoperiodontitis and peri-implantitis Interdental brush coated with composition effective for alleviating and preventing symptoms of gingivoperiodontitis and peri-implantitis

FIG. 1

Before applying composition effective for alleviating and preventing symptoms of gingivoperiodontitis and peri-implantitis After applying composition effective for alleviating and preventing symptoms of gingivoperiodontitis and peri-implantitis

FIG. 2

Inflammation and bleeding around implant fixture application of composition

2 days after application of composition, inflammation reduction (yellow arrow)

6 days after application of composition, inflammation eliminated (yellow arrow)

2 weeks after application of composition, crown is mounted again

X-ray image 2 weeks after application of composition

FIG. 3

Plaque around orthodontic device can be seen when treated with a disclosing solution

Composition was applied to plaque and inflammation under orthodontic device.

Rubbing using micro-brush for 1-2 minutes

Removal of remaining composition with swab

Washing with saline

After 1 week, plaque and gum inflammation were removed

SEQUENCE LISTING

<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Antimicrobial Peptide

```
<400> SEQUENCE: 1

Gly Lys Cys Ser Thr Arg Gly Arg Lys Cys Cys Arg Arg Lys Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Antimicrobial Peptide

<400> SEQUENCE: 2

Gly Lys Ser Ser Thr Arg Gly Arg Lys Ser Cys Arg Arg Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Antimicrobial Peptide

<400> SEQUENCE: 3

Gly Lys Cys Ser Thr Arg Gly Arg Lys Ser Ser Arg Arg Lys Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Antimicrobial Peptide

<400> SEQUENCE: 4

Gly Lys Ser Ser Thr Arg Gly Arg Lys Cys Ser Arg Arg Lys Lys
1               5                   10                  15
```

COMPOSITION FOR TREATING AND PREVENTING GINGIVOPERIODONTITIS OR PERI-IMPLANTITIS, AND INTERDENTAL BRUSH COATED WITH SAME

TECHNICAL FIELD

The present invention relates to a composition for treating and preventing gingivoperiodontitis or peri-implantitis, and an interdental brush coated with the composition, and more particularly to a composition for treating and preventing gingivoperiodontitis or peri-implantitis containing, as active ingredients, sodium ethylenediaminetetraacetate, cetylpyridinium chloride, octyl phenol ethoxylate and sodium bicarbonate, and an interdental brush coated with the composition.

BACKGROUND ART

Periodontal disease is often referred to as gum disease, and is divided into gingivitis and periodontitis depending on the severity of the disease. Gingivitis is a periodontal disease that is relatively mild and from which recovery is quick, and is limited to the gums, that is, soft tissues, and periodontitis is a periodontal disease wherein inflammation progresses to the gums and bones around the gums. A V-shaped gap called a "sulcus" forms between the gingiva (gum) and the tooth, and bacteria attack the part below the gingival line of the sulcus, damaging the periodontal ligament and adjacent tissues. As inflammation progresses and more tissue is damaged, the sulcus grows into a periodontal pocket. As periodontitis becomes severe, the periodontal pocket becomes deeper. As the periodontal pocket deepens, the periodontal ligament becomes inflamed, and bone loss may occur, which results in tooth loss. The cause of periodontal disease is a bacterial membrane called "plaque" formed on teeth, and the types of bacteria include *Prevotella intermedia, Actinomyces israelii, Fusobacterium nucleatum* and the like.

Meanwhile, peri-implantitis is a disease in which the gums and gum bones are inflamed around an implant. As society ages, the number of implants is increasing, so the incidence of peri-implantitis is also increasing. Initial peri-implantitis causes inflammation only in the gums around the implant, and when it becomes severe, a phenomenon like periodontitis, in which the gum bones are absorbed, occurs. However, implants have no periodontal ligaments and nerves present in natural teeth, thus causing more destructive inflammatory reactions than natural teeth. The bacteria directly causative of peri-implantitis are similar to the bacteria found in periodontitis.

In order to treat periodontal disease and peri-implantitis, efforts to remove the causative bacteria that form the tooth surface bacterial membrane by administering antibiotics are ongoing, but there is a problem in that the antibiotics cannot be used in clinical practice due to the production of antibiotic-resistant bacteria upon long-term use. In order to overcome this problem, various methods such as the use of a fluorine compound or an automatic tooth-cleaning device have been developed, but no great results in terms of effectiveness have been obtained. In addition, chlorhexidine, which is widely used in addition to antibiotics, is a liquid and thus has a disadvantage of exerting an effect only for a short period and causing discoloration of the teeth when used for a long time.

Procedural methods for regeneration of tissue destroyed by periodontal disease and for removal of bacteria include calculus removal (scaling) and root planing. However, after mechanical cleaning, a bacterial layer is formed on the root surface, which may inhibit fibroblast adhesion and connective tissue adhesion, and is provided as a substrate on which bacteria can proliferate and interfere with the healing of periodontal tissue. For this reason, research has been made on root treatment methods using a tooth root cleaner (KR 10-1453206B1). Research is underway on drugs for removing bacteria along with toxic substances induced by bacteria during mechanical treatment, such as citric acid, fibronectin, tetracycline hydrochloride (Tc—HCl), phosphoric acid, stannous fluoride, ethylene tetraacetic diamine acid (EDTA), chlorhexidine, formalin, cetylpyridinium chloride, sodium-N-lauroyl sarcosine, zinc iontophoresis and the like.

However, conventional antibacterial drugs (for example, KR 10-0621191, KR 10-0978822 B1) are acidic in liquid and thus irritate the gums. These drugs are used through a process in which patients visit the hospital and are treated by doctors. For this reason, it is difficult for the patient to use these drugs for continuous maintenance and management purposes. Currently, most agents for relieving and preventing symptoms of gingivoperiodontitis and peri-implantitis that can be used at home are toothpastes and gargles, and the effects and persistence thereof are not great. Since periodontal disease is difficult to treat if not initially responded to, regular management and prevention therefor are important. Thus, there is a need for a drug that relieves symptoms and prevents gingivoperiodontitis and peri-implantitis and is easily used by a patient at home.

Accordingly, as a result of extensive efforts to solve the problems of the prior art, the present inventors have developed a composition that can alleviate and prevent symptoms peri-implantitis, and of gingivoperiodontitis and an interdental brush coated with the composition in a form convenient for patients to use after brushing, and found that, when the composition and the interdental brush coated with the composition were used in clinical practice, an effect of alleviating gingivoperiodontitis and peri-implantitis could be obtained. Based on this finding, the present invention has been completed.

DISCLOSURE

Therefore, the present invention has been made in view of the above problems, and it is one object of the present invention to provide a composition having an effect of alleviating and preventing symptoms of gingivoperiodontitis and peri-implantitis, the use of the composition, and a method for treating and preventing the symptoms using the composition.

In accordance with one aspect of the present invention, the above and other objects can be accomplished by the provision of a composition for treating and preventing gingivoperiodontitis or peri-implantitis comprising, as active ingredients, sodium ethylenediaminetetraacetate, cetylpyridinium chloride, octyl phenol ethoxylate and sodium bicarbonate.

In accordance with another aspect of the present invention, provided is an interdental brush coated with the composition.

In accordance with another aspect of the present invention, provided is an implant crown coated with the composition.

In accordance with another aspect of the present invention, provided is an orthodontic device coated with the composition.

In accordance with another aspect of the present invention, provided is a method for treating gingivoperiodontitis or peri-implantitis comprising applying the composition between the teeth, around an implant or around an orthodontic device of a subject in need of treatment, or cleaning between the teeth, around the implant or around the orthodontic device of the subject in need of treatment with the composition.

In accordance with another aspect of the present invention, provided is the use of the composition for treatment of gingivoperiodontitis or peri-implantitis.

In accordance with another aspect of the present invention, provided is the use of the composition for preparation of a therapeutic drug for gingivoperiodontitis or peri-implantitis.

BEST MODE

Unless defined otherwise, all technical and scientific terms used herein have the same meanings as appreciated by those skilled in the field to which the present invention pertains. In general, the nomenclature used herein is well-known in the art and is ordinarily used.

The present invention is based on the finding that, when the composition containing, as active ingredients, sodium ethylenediaminetetraacetate, cetylpyridinium chloride, octyl phenol ethoxylate and sodium bicarbonate and the interdental brush coated with the composition are used in clinical practice, the effect of alleviating symptoms of gingivoperiodontitis and peri-implantitis can be obtained.

In one aspect, the present invention is directed to a pharmaceutical composition for treating and preventing gingivoperiodontitis or peri-implantitis comprising, as active ingredients, sodium ethylenediaminetetraacetate, cetylpyridinium chloride, octyl phenol ethoxylate and sodium bicarbonate.

Sodium ethylenediaminetetraacetate is a substance that forms a chelate with a divalent cation such as $Ca^{2+}$, $Mg^{2+}$, $Fe^{2+}$ and $Pb^{2+}$ at a neutral pH, and reacts with calcium ions in dentine to produce calcium complex salts to thereby remove the bacterial layer produced upon root surface planing, exposes fresh collagen substrates to promote the movement of fibroblasts by chemotaxis, and provide a place where biologically active growth factors are maintained. Therefore, in the present invention, sodium ethylenediaminetetraacetate has an effect of removing minerals present on the root surface and an antimicrobial effect.

Octyl phenol ethoxylate $(C_{14}H_{22}O(C_2H_4O)_n)$ is a nonionic surfactant, has a hydrophilic polyethylene oxide group and a hydrophobic 4-(1,1,3,3-tetramethylbutyl)-phenyl group, and is widely used as a detergent in the biochemical field. In immunostaining, octyl phenol ethoxylate permeabilizes the cell membrane at a concentration of 0.1 to 0.5%, and permeabilizes the cell wall of bacteria at a concentration of 1%. In the present invention, octyl phenol ethoxylate has an effect of removing lipopolysaccharide (LPS). Other non-ionic surfactants widely used in this technical field include polyoxyethylene, Tween series, span series and the like. However, the result of testing the removal effect of lipopolysaccharides showed that octyl phenol ethoxylate exhibits the greatest lipopolysaccharide removal effect.

In the present invention, cetylpyridinium chloride is a tetravalent ammonium compound that has effects of killing bacteria and microorganisms, and reducing tooth plaque and gum inflammation.

In the present invention, sodium bicarbonate has pH control and polishing effects.

In the present invention, the composition for treating and preventing gingivoperiodontitis or peri-implantitis comprisies 15 to 30 parts by weight of the sodium ethylenediaminetetraacetate, 1 to 2 parts by weight of the octyl phenol ethoxylate, 0.01 to 1 parts by weight of the cetylpyridinium chloride, and 1 to 10 parts by weight of the sodium bicarbonate, based on 100 parts by weight of the composition.

When the content of sodium ethylenediaminetetraacetate is less than 15 parts by weight, the demineralization effect is not great, and when the content exceeds 30 parts by weight, the demineralization effect does not increase, so there is no actual benefit from the increased content. In addition, when the content of octyl phenol ethoxylate is less than 1 part by weight, the effect of removing lipopolysaccharides does not occur, and when the content exceeds 2 parts by weight, the effect of removing lipopolysaccharides does not increase, so there is no actual benefit from the increased content. When the content of cetylpyridinium chloride is less than 0.01 parts by weight, there is no antimicrobial effect, and when the content exceeds 1 part by weight, the antimicrobial effect does not increase, so there is no actual benefit from the increased content. When the content of sodium bicarbonate is less than 1 part by weight, pH control and polishing effects are not great, and when the content exceeds 10 parts by weight, the tooth is abraded, so there is no actual benefit from the increased content.

In the present invention, the composition may further comprise an antimicrobial peptide. The antimicrobial peptide is selected from the group consisting of human alpha-defensin (α-defensin), human beta-defensin (β-defensin), cathelicidin, LL-37, and histatin, but is not limited thereto.

Antimicrobial peptides are present in the human innate immune system, and bind to and puncture cell membranes, thereby exhibiting a wide range of antimicrobial activity against bacteria, fungi and viruses (Brogden K. A. Antimicrobial peptides: pore formers or metabolic inhibitors in bacteria. *Nat. Rev. Microbiol.* 2005; 3:238.50, Sørensen O. E. et al., Antimicrobial peptides in innate immune responses, Contrib. Microbiol. 2008; 15:61.77). In addition, some of the antimicrobial peptides function to neutralize the activity of LPS (Rosenfeld Y., Papo N., Shai Y. Endotoxin (lipopolysaccharide) neutralization by innate immunity host-defense peptides, Peptide properties and plausible modes of action, *J. Biol. Chem.* 2006; 281:163643).

Antimicrobial peptides are produced in various cells related to infection, such as epithelial cells, neutrophils and salivary glands. There are human defensins, cathelicidin, LL-37, histatin and the like. The peptides are positively charged and are known to prevent sepsis and inflammation caused by Gram-negative and Gram-positive bacteria (Scott M. G. et al., Interaction of cationic peptides with lipoteichoic acid and Gram-positive bacteria, *Infect. Immun.* 1999; 67:6445.53, Giacometti A. et al., Potential therapeutic role of cationic peptides in three experimental models of septic shock, Antimicrob. Agents Chemother. 2002; 46:2132.6).

Meanwhile, the antimicrobial peptide may be selected from the group consisting of antimicrobial peptides represented by the amino acid sequences of SEQ ID NO: 1 to SEQ ID NO: 4, but is not limited thereto. In this case, the antimicrobial peptide represented by the amino acid sequence of SEQ ID NO: 2 exhibits the best antimicrobial activity and is thus particularly preferably used in the composition of the present invention.

SEQ ID NO: 1 Peptide GKCST RGRKC CRRKK-NH2
SEQ ID NO: 2 Peptide GKSST RGRKS CRRKK-NH2
SEQ ID NO: 3 peptide GKCST RGRKS SRRKK-NH2
SEQ ID NO: 4 Peptide GKSST RGRKC SRRKK-NH2

In the present invention, the antimicrobial peptide may be present in an amount of $1 \times 10^{-5}$ to $1 \times 10^{-3}$ parts by weight based on 100 parts by weight of the composition. The reason for this is that, when the antimicrobial peptide is present in an amount of less than $1 \times 10^{-5}$ parts by weight, the antimicrobial effect is not great, and when the antimicrobial peptide is present in an amount of more than $1 \times 10^{-3}$ parts by weight, the antimicrobial effect does not increase, and thus there is no actual benefit from the increased content.

In the present invention, the composition may further contain one or more selected from the group consisting of propolis, xylitol and proteolytic enzymes. By further containing propolis or xylitol, it is possible to improve sensory properties, and by further containing the proteolytic enzymes, the antimicrobial effect and lipopolysaccharide removal effect can be increased.

The composition of the present invention may further contain a pharmaceutically acceptable carrier, and examples of the pharmaceutically acceptable carrier that is used include excipients (e.g., starch, lactose, calcium carbonate, calcium phosphate, etc.), binders (e.g., starch, gum arabic, carboxymethylcellulose, hydroxymethyl cellulose, crystalline cellulose, etc.), lubricants (e.g., magnesium stearate, talc, etc.), disintegrants (e.g., carboxymethylcellulose calcium, talc synthetic aluminum silicate, etc.), diluents (e.g., water, vegetable oil, etc.), and a mixture of two or more thereof.

The formulation of the composition according to the present invention is not particularly limited, but is most preferably formulated as a granule, microgranule, liquid, powder, spray, ointment or gel, and is most preferably formulated as a gel.

In another aspect, the present invention is directed to an interdental brush coated with the composition.

The interdental brush may be coated with 0.01 to 0.04 g of the composition. When the weight of the coated composition is less than 0.01 g, the bristle is not properly coated therewith, and when the weight of the coated composition exceeds 0.04 g, the coating layer is peeled off due to excessive coating.

In another aspect, the present invention is directed to an implant crown coated with the composition.

The implant crown may be coated with 0.05 to 0.2 g of the composition.

In another aspect, the present invention is directed to an orthodontic device coated with the composition.

The orthodontic device may be coated with 0.01 to 0.1 g of the composition.

In another aspect, the present invention is directed to the use of the composition for the treatment and prevention of gingivoperiodontitis or peri-implantitis. That is, the present invention provides the use of the composition for the treatment of gingivoperiodontitis or peri-implantitis. In another aspect, the present invention is directed to the use of the composition for the preparation of a therapeutic drug for gingivoperiodontitis or peri-implantitis.

In another aspect, the present invention is directed to a method for treating and preventing gingivoperiodontitis or peri-implantitis using the composition and the interdental brush coated with the composition. That is, the present invention is directed to a method for treating gingivoperiodontitis or peri-implantitis comprising applying the composition between the teeth, around an implant or around an orthodontic device of a subject in need of treatment, or cleaning between the teeth, around the implant or around the orthodontic device of the subject in need of treatment with the composition.

In one embodiment of the present invention, the treatment/prevention method may comprise cleaning between the teeth, around the implant or around the orthodontic device using a soft brush having the composition applied thereto, or using an interdental brush coated with the composition. In this case, cleaning is performed 1 to 2 times a day for 1 to 3 weeks.

In another embodiment of the present invention, the method comprises (a) coating an implant crown with the composition, and (b) implanting the coated implant crown. In the present invention, the step (a) may comprise performing coating before initial implantation of the implant or re-implantation of an implant crown separated from a peri-implantitis patient. The amount of the composition used for coating the implant crown is 0.05 to 0.2 g, but is not limited thereto.

In another embodiment of the present invention, the method comprises (a) removing the implanted crown, and (b) applying the composition around the site from which the implant crown has been removed. The amount of the composition applied around the site from which the implant crown has been removed is 0.05 to 0.2 g, but is not limited thereto. In this case, the composition may be applied using a brush with soft and fine hair to minimize irritation to the inflamed area.

In another embodiment of the present invention, the method comprises (a) coating an orthodontic device with the composition, and (b) mounting the coated orthodontic device on the teeth. The amount of the composition for coating the orthodontic device is 0.01 to 0.1 g, but is not limited thereto.

In another embodiment of the present invention, an orthodontic device mounted on the teeth may be coated with the composition. The amount of the composition used for coating the orthodontic device may be 0.01 to 0.1 g, but is not limited thereto.

In the present invention, the coating is a method of applying a sufficient amount of the composition of the present invention to the surface of the interdental brush, implant crown and the orthodontic device to maintain the composition thereon for a certain period of time. Simply, the coating is carried out by immersing an area of the interdental brush, implant crown and orthodontic device in need of coating in the composition of the present invention for 1 second to 10 minutes. Alternatively, the coating may be carried out by evenly spreading or applying the composition of the present invention to an area of the interdental brush, implant crown and orthodontic device in need of coating using a brush or the like.

EXAMPLE

Hereinafter, the present invention will be described in more detail with reference to examples. However, it will be obvious to those skilled in the art that these examples are provided only for illustration of the present invention and should not be construed as limiting the scope of the present invention.

Figure 1:
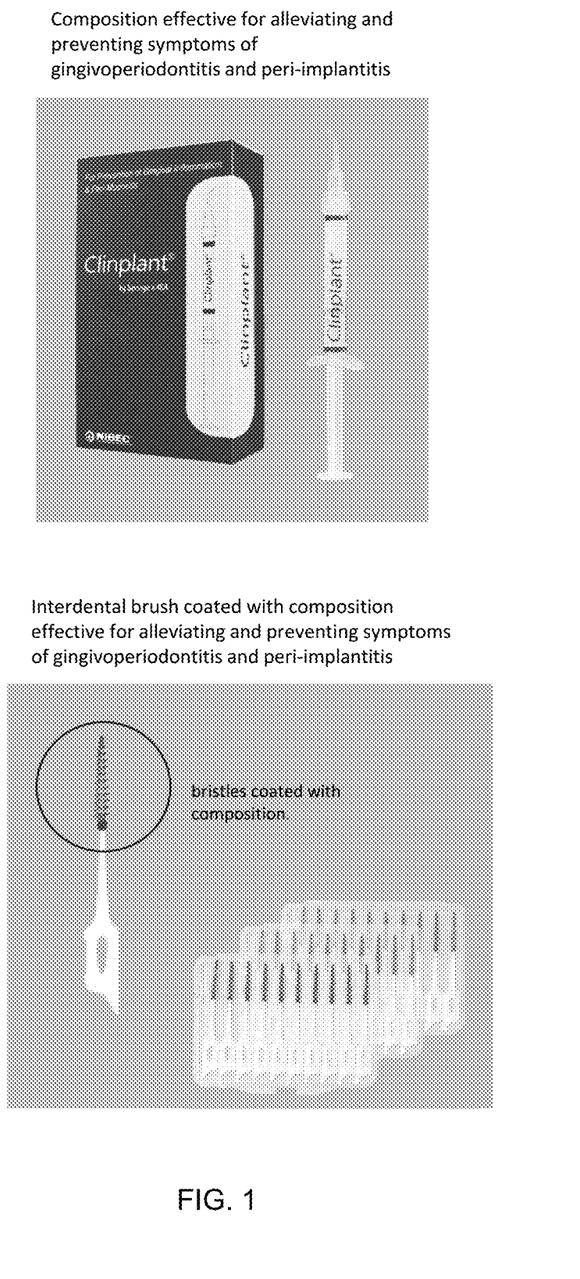
FIG. 1 is an image showing a composition effective for alleviating and preventing symptoms of gingivoperiodontitis and peri-implantitis according to the present invention and an interdental brush coated with the composition.

Example 1: Preparation of Composition Effective for Alleviating and Preventing Symptoms of Gingivoperiodontitis and Peri-Implantitis 1.5 g of sodium carboxymethyl cellulose and 1 g of L-menthol as a flavoring agent were dissolved in 73.45 g of purified water at about 100° C. to prepare a primary mixture, and 17 g of disodium ethylene diaminetetraacetate dihydrate (EDTA-2Na-2H$_2$O) was secondarily mixed with the primary mixture at about 100° C. 1 g of Triton X-100 (Sigma, USA), which is octyl phenol ethoxylate, 5 g of sodium bicarbonate, 1 g of xylitol, and 0.05 g of cetyl pyridinium chloride (CPC) were added to and mixed with the secondary mixed solution to prepare a composition effective for alleviating and preventing symptoms of gingivoperiodontitis and peri-implantitis, and then a syringe was filled with the composition (FIG. 1).

Example 2: Production of Interdental Brush Coated with Composition Effective for Alleviating and Preventing Symptoms of Gingivoperiodontitis and Peri-Implantitis The dental cleanser interdental brush is provided in a set of 10. Before coating with the composition of Example 1, the weight of a set of (10) dental cleanser interdental brushes was measured with a scale. The bristles of the interdental brush were completely immersed in an airtight container containing the composition of Example 1 on a clean bench (BSC type), allowed to stand upside down until the composition did not fall therefrom, and were then thoroughly dried on a clean bench (BSC type) while standing in a drying rack. The weight of the dried interdental brush was measured with a scale and the weight before and the weight after coating were compared to detect the coated amount.

TABLE 1

Calculation of the amount of composition used for coating interdental brush (10 ea/set)

| No. | Weight of interdental brush before coating (g) | Weight of interdental brush after coating (g) | Increase in weight = amount of composition coated (g) |
|---|---|---|---|
| 1 | 1.2697 | 1.4497 | 0.18 |
| 2 | 1.3209 | 1.493 | 0.1721 |
| 3 | 1.2752 | 1.4703 | 0.1951 |
| 4 | 1.2722 | 1.4396 | 0.1674 |
| 5 | 1.2741 | 1.4653 | 0.1912 |
| 6 | 1.2762 | 1.4075 | 0.1313 |
| 7 | 1.3217 | 1.4513 | 0.1296 |
| 8 | 1.2703 | 1.4125 | 0.1422 |
| 9 | 1.3206 | 1.4448 | 0.1242 |
| 10 | 1.2734 | 1.429 | 0.1556 |
| 11 | 1.3157 | 1.4588 | 0.1431 |
| 12 | 1.2699 | 1.4312 | 0.1613 |
| 13 | 1.3204 | 1.4622 | 0.1418 |
| 14 | 1.2762 | 1.4421 | 0.1659 |
| 15 | 1.3205 | 1.4305 | 0.11 |
| 16 | 1.2731 | 1.4671 | 0.194 |
| 17 | 1.2762 | 1.4421 | 0.1659 |
| 18 | 1.2829 | 1.45271 | 0.16981 |
| 19 | 1.3104 | 1.46121 | 0.15081 |
| 20 | 1.3147 | 1.4598 | 0.1451 |
| | Average | | 0.156821 (0.0146821 per interdental brush) |

Figure 2:
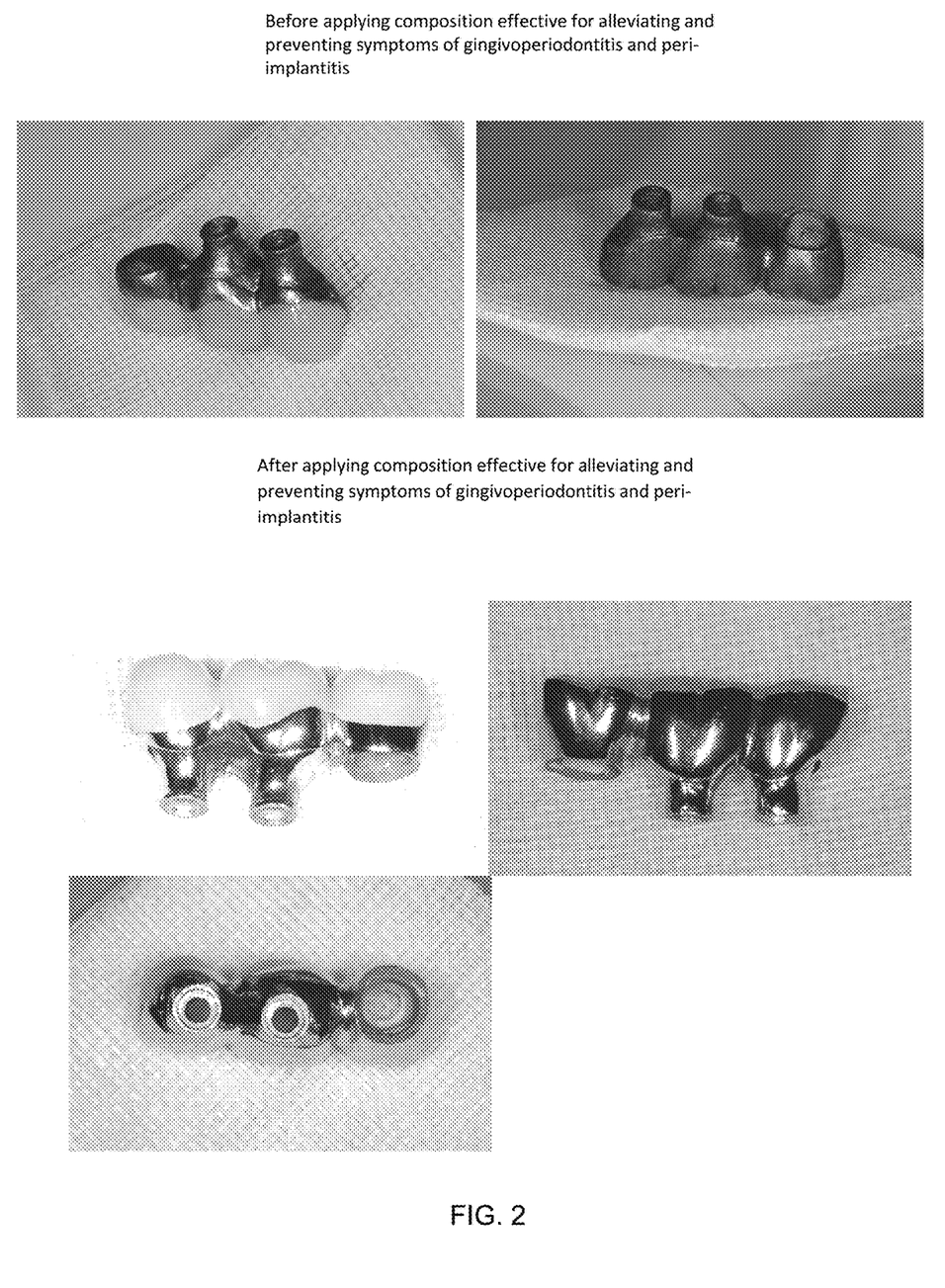
FIG. 2 is an image showing that bacteria are removed by applying the composition according to an example of the present invention to a crown mounted on an implant contaminated by bacteria.

Experimental Example 1: Effect of Removing Bacteria by Implant Crown to which Composition Effective for Alleviating and Preventing Symptoms of Gingivoperiodontitis and Peri-Implantitis is Applied An implant crown was detached from a patient with peri-implantitis and the degree of bacterial contamination was observed using a disclosing solution. The composition of Example 1 was applied to the surface of the implant crown, allowed to stand for 1 to 2 minutes, and washed with saline. FIG. 2 is an image showing the states before and after applying the composition to the implant crown. Before coating the composition, the implant crown was dyed red, whereas after cleaning using the composition, the implant was not dyed due to the tooth colorant, which proves that bacteria and contaminants were completely removed.

Figure 3:
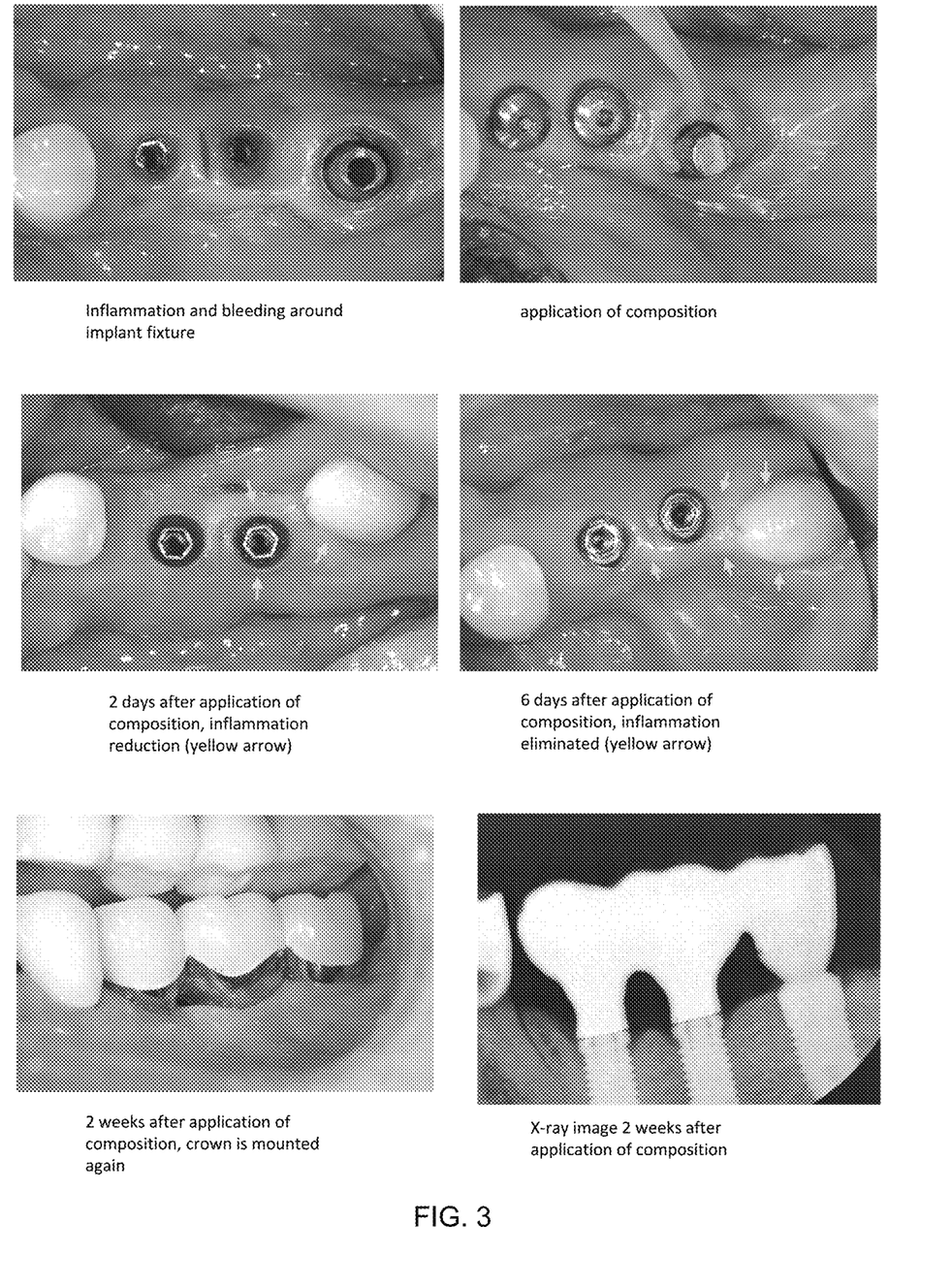
FIG. 3 is a clinical image showing the effect of reducing swelling and bleeding symptoms of the gums when using the composition according to an example of the present invention in an implant fixture.

Experimental Example 2: Clinical Effect on Peri-Implantitis Patients Using Composition Effective for Alleviating and Preventing Symptoms of Gingivoperiodontitis and Peri-Implantitis An implant crown was removed from a patient who had peri-implantitis among patients who received implants (FIG. 3), and the composition of Example 1 was applied thereto (FIG. 3). The result of observation 2 days, 6 days and 2 weeks after application of the composition showed that inflammation, swelling and bleeding around the implant decreased over time. Two weeks after application of the composition, the inflammation was completely eliminated and the implant crown could be remounted. This proves that the composition of Example 1 is effective against peri-implantitis.

Figure 4:
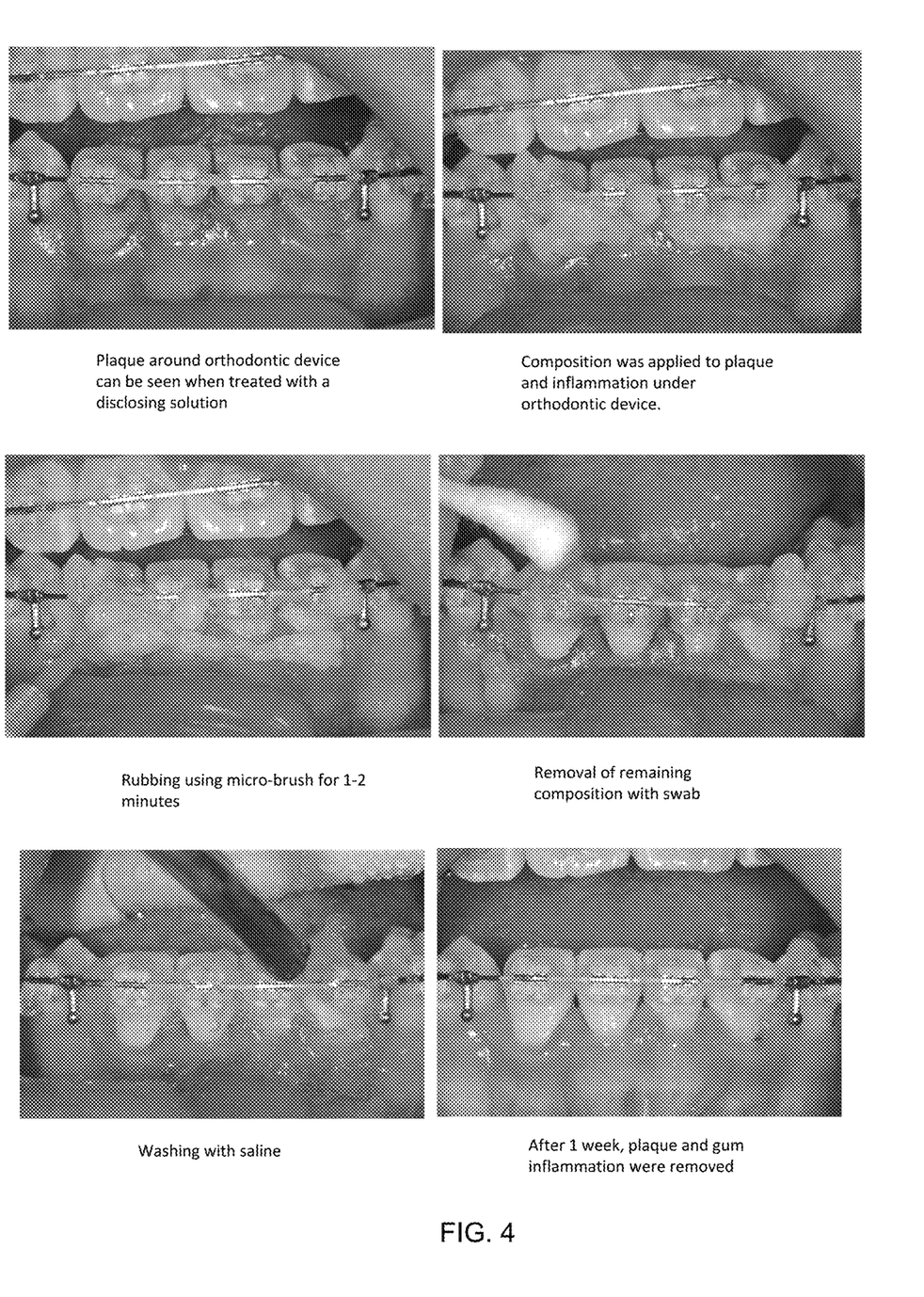
FIG. 4 is a clinical image showing the effects of removing bacteria around the orthodontic device and alleviating gum inflammation after applying the composition according to an example of the present invention to the orthodontic device.

Experimental Example 3: Clinical Effect on Patients with Orthodontic Device Using Composition Effective for Alleviating and Preventing Symptoms of Gingivoperiodontitis and Peri-Implantitis The composition of Example 1 was applied to patients suffering from severe gum inflammation and plaque, among patients with orthodontic devices (FIG. 4). When the area around the orthodontic device was dyed, it was dyed red. The composition of Example 1 was applied around the orthodontic device and rubbed with a microbrush, and the remaining composition was washed with a cotton swab and saline. One week later, observation was conducted again. The result showed that removal of plaque and inflammation was detected. This proves that the composition of Example 1 is effective in removing plaque and reducing inflammation of the gums.

Figure 5:
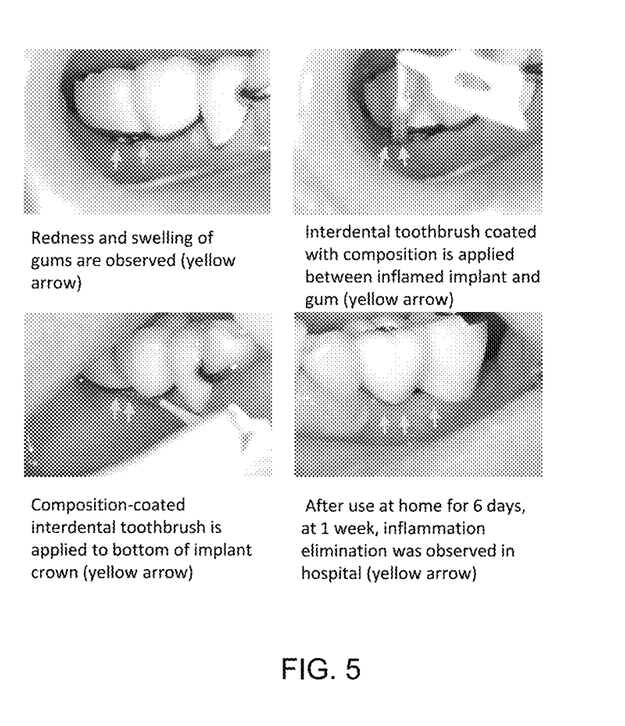
FIG. 5 is a clinical image showing the effect of alleviating gum inflammation when the interdental brush coated with the composition according to an example of the present invention is used under the implant crown.

Experimental Example 4: Clinical Effect on Patients with Peri-Implantitis Using Interdental Brush Coated with Composition Effective for Alleviating and Preventing Symptoms of Gingivoperiodontitis and Peri-Implantitis The interdental brush coated with the composition of Example 2 was applied to patients suffering from severe gum inflammation and plaque, among patients who received implants (FIG. 5). Each patient used an interdental brush coated with the composition of Example 2 at home once a day over 6 days and visited the hospital one week later. The result of observation showed that the inflammation around the implant was removed. This proves that the interdental brush coated with the composition of Example 2 is effective against peri-implantitis.

Experimental Example 5: Improvement of Efficacy Due to Addition of Antimicrobial Peptide The antimicrobial peptide was further added to the composition of Example 1 in order to induce an improvement in efficacy, and the following peptides were used for this purpose.
SEQ ID NO: 1 Peptide GKCST RGRKC CRRKK-NH2
SEQ ID NO: 2 Peptide GKSST RGRKS CRRKK-NH2
In order to determine the effect of the composition containing the antimicrobial peptide, an antimicrobial experiment was conducted according to the liquid dilution method. *Prevotella intermedia*, which is a bacterium causative of periodontal disease, was cultured in Tryptic soy broth. The above strain was cultured until the absorbance at 620 nm reached 1, and then the cells were collected and used in the experiment. The cells were diluted with PBS, bacteria were plated at 105-107/mL on a tryptic soy agar (TSA) plate, and incubated at 37° C. for 24 hours. In order to measure the antimicrobial activity of the peptides using a liquid dilution method, 1 ml of distilled water was added to a microtube, 10 µl of diluted bacterial solution was added thereto and 50 µl of the product was plated on a plate medium which was used as a control group.

After treatment with 50 µg/ml and 100 µg/ml of the peptide of SEQ ID NO: 1 and 50 µg/ml and 100 µg/ml of the peptide of SEQ ID NO: 2 at 37° C. for 1 hour, 50 µl of each of the product was plated and the number of colonies that formed was counted. In addition, the antimicrobial activity of the composition of Example 1, a composition containing the composition of Example 1 and the peptide of SEQ ID NO: 1, and a composition containing the composition of Example 1 and the peptide of SEQ ID NO: 2 was measured in the same manner as above.

Figure 6:
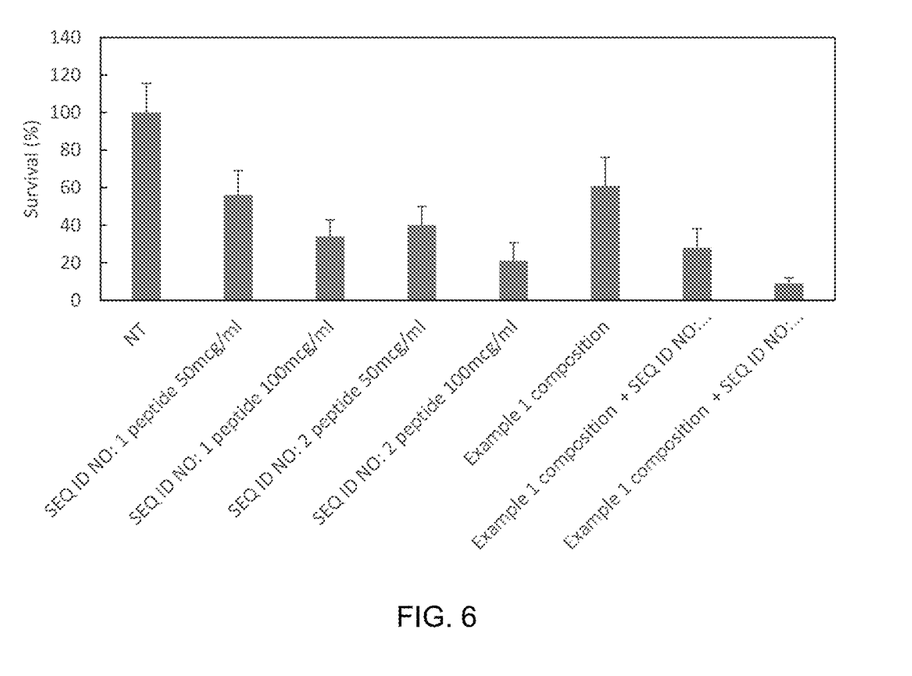
FIG. 6 shows the antimicrobial activity of a composition according to an example of the present invention to which an antimicrobial peptide is further added.

As a result, as shown in FIG. 6, the antimicrobial activity when the peptide of SEQ ID NO: 2 was added at a concentration of 100 µg/ml was the highest, and was better than when the peptide of SEQ ID NO: 1 was added at the same concentration. In addition, the antimicrobial effect was increased further the was when antimicrobial peptide additionally added, compared to when only the composition of Example 1 was used. In particular, the antimicrobial effect of the composition mixed with the peptide of SEQ ID NO: 2 was increased even further.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The composition according to the present invention effectively removes bacteria that cause gingivoperiodontitis and peri-implantitis, thereby relieving inflammation, and the interdental brush coated with the composition is easily applied between the teeth, to implants and to orthodontic devices, thus enabling easy treatment and prevention of gingivoperiodontitis and peri-implantitis at home. Inflamed areas as well as implant crowns and orthodontic devices of patients can be directly coated with the composition, so the composition can act on inflamed areas for a longer time compared to the case of direct application to inflamed areas, and can promote inflammation relief. In addition, the composition has effects of removing inflammation-causing bacteria present on implant crowns and orthodontic devices, which are not removed by brushing, and thus of preventing gingivoperiodontitis and peri-implantitis.

[Sequence Free Text]
An electronic file is attached.

The invention claimed is:

1. A method for treating and preventing gingivoperiodontitis or peri-implantitis comprising applying a pharmaceutical composition comprising sodium ethylenediaminetetraacetate, cetylpyridinium chloride, octyl phenol ethoxylate, sodium bicarbonate, and an antimicrobial peptide between the teeth, around an implant or around an orthodontic device of a subject in need of treatment, or cleaning between the teeth, around the implant or around the orthodontic device of the subject in need of treatment with the composition; wherein the antimicrobial peptide is selected from the group consisting of antimicrobial peptides represented by the amino acid sequences of SEQ ID NO: 2 to SEQ ID NO: 4.

2. The method according to claim 1, wherein the pharmaceutical composition comprises 15 to 30 parts by weight of the sodium ethylenediaminetetraacetate, 1 to 2 parts by weight of the octyl phenol ethoxylate, 0.01 to 1 parts by weight of the cetylpyridinium chloride, and 1 to 10 parts by weight of the sodium bicarbonate, based on 100 parts by weight of the composition.

3. The method according to claim 1, wherein the antimicrobial peptide is present in an amount of $1\times10^{-5}$ to $1\times10^{-3}$ parts by weight based on 100 parts by weight of the composition.

4. An interdental brush coated with a composition comprising sodium ethylenediaminetetraacetate, cetylpyridinium chloride, octyl phenol ethoxylate, sodium bicarbonate, and an antimicrobial peptide, wherein the antimicrobial peptide is selected from the group consisting of antimicrobial peptides represented by the amino acid sequences of SEQ ID NO: 2 to SEQ ID NO: 4.

5. The interdental brush according to claim 4, wherein the interdental brush is coated with 0.01 to 0.04 g of the composition.

6. An implant crown coated with a composition comprising sodium ethylenediaminetetraacetate, cetylpyridinium chloride, octyl phenol ethoxylate, sodium bicarbonate, and an antimicrobial peptide, wherein the antimicrobial peptide is selected from the group consisting of antimicrobial peptides represented by the amino acid sequences of SEQ ID NO: 2 to SEQ ID NO: 4.

7. The implant crown according to claim 6, wherein the implant crown is coated with 0.05 to 0.2 g of the composition.

8. An orthodontic device coated with a composition comprising sodium ethylenediaminetetraacetate, cetylpyridinium chloride, octyl phenol ethoxylate, sodium bicarbonate, and an antimicrobial peptide, wherein the antimicrobial peptide is selected from the group consisting of antimicrobial peptides represented by the amino acid sequences of SEQ ID NO: 2 to SEQ ID NO: 4.

9. The orthodontic device according to claim 8, wherein the orthodontic device is coated with 0.01 to 0.1 g of the composition.

* * * * *